United States Patent [19]

Ponsford et al.

[11] 4,410,533

[45] Oct. 18, 1983

[54] β-LACTAM ANTIBIOTICS, THEIR PREPARATION AND USE

[75] Inventors: Roger J. Ponsford, Horsham; Pamela Brown, Guildford; Steven Coulton, Horsham, all of England

[73] Assignee: Beecham Group p.l.c., England

[21] Appl. No.: 345,485

[22] Filed: Feb. 3, 1982

[30] Foreign Application Priority Data

Feb. 4, 1981 [GB] United Kingdom ............... 8103348

[51] Int. Cl.³ ................. C07D 487/04; A61K 31/505
[52] U.S. Cl. .............................. 424/251; 260/245.2 T; 424/274; 544/316; 544/317; 544/319; 544/320
[58] Field of Search ................. 260/245.2 T; 544/316, 544/317, 319, 320; 424/251, 274

[56] References Cited

U.S. PATENT DOCUMENTS

| | | | |
|---|---|---|---|
| 4,189,493 | 2/1980 | Christensen et al. | 260/245.2 T |
| 4,309,346 | 1/1982 | Christensen et al. | 260/245.2 T |
| 4,323,569 | 4/1982 | Baxter | 260/245.2 T |
| 4,337,199 | 6/1982 | Yoshioka et al. | 260/245.2 T |
| 4,347,367 | 8/1982 | Christensen et al. | 260/245.2 T |

*Primary Examiner*—Mary C. Lee
*Attorney, Agent, or Firm*—Jacobs & Jacobs

[57] ABSTRACT

The present invention provides a compound of the formula (I):

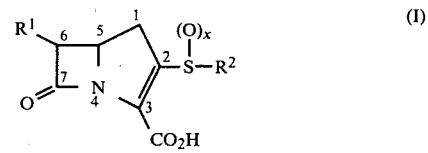

or a pharmaceutically acceptable salt or in-vivo hydrolyzable ester thereof wherein $R^1$ is a hydrogen atom, an α-sulphonato-oxyethyl group, an α-sulphonato-oxypropyl group or is a group $CR^3R^4R^5$ wherein $R^3$ is a hydrogen atom or a hydroxy group; $R^4$ is a hydrogen atom or a $C_{1-6}$ alkyl group; and $R^5$ is a hydrogen atom or a $C_{1-6}$ alkyl group, a benzyl group, a phenyl group or is joined to $R^4$ to form together with the carbon atom to which they are joined a carbocyclic ring of 5 to 7 carbon atoms; $R^2$ is a pyrimidinyl group substituted by one two or three groups selected from nitro, halo, amino or substituted amino, and in addition may be optionally substituted by one or two $C_{1-6}$ alkyl groups as the degree of substitution permits; and x is zero or one.

These compounds are antibacterial agents. Their preparation and use are described.

10 Claims, No Drawings

β-LACTAM ANTIBIOTICS, THEIR PREPARATION AND USE

This invention relates to novel carbapenem derivatives and in particular to 3-substituted thio carbapenem derivatives. This invention further relates to processes for their preparation and to compositions containing them.

European patent application No. 0001627, 0001628, 0008514, 017970 and 017992 disclose a wide variety of carbapenem derivatives.

We have discovered a novel class of antibiotics not specifically disclosed in any of the aforementioned publications. These compounds have superior efficacy, for example antibacterial activity and/or stability, than related compounds specifically disclosed in the aforementioned publications.

Accordingly, the present invention provides a compound of the formula (I):

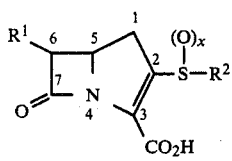

or a pharmaceutically acceptable salt or in-vivo hydrolysable ester thereof wherein $R^1$ is a hydrogen atom, an α-sulphonato-oxyethyl group, an α-sulphonato-oxypropyl group or is a group $CR^3R^4R^5$ wherein $R^3$ is a hydrogen atom or a hydroxy group; $R^4$ is a hydrogen atom or a $C_{1-6}$ alkyl group; and $R^5$ is a hydrogen atom or a $C_{1-6}$ alkyl group, a benzyl group, a phenyl group or is joined to $R^4$ to form together with the carbon atom to which they are joined a carbocyclic ring of 5 to 7 carbon atoms; $R^2$ is a pyrimidinyl group substituted by one two or three groups selected from nitro, halo, amino or substituted amino, and in addition may be optionally substituted by one or two $C_{1-6}$ alkyl groups as the degree of substitution permits; and x is zero or one.

Suitably x is zero. Suitably x is one.

When used herein "halo" means chloro, bromo or iodo, preferably chloro or bromo. "Substituted amino" includes $C_{1-6}$ alkylamino such as methylamino or ethylamino; $C_{2-6}$ alkylamido such as acetamido or propionamido; aryl ($C_{2-6}$) alkylamido wherein aryl is suitably phenyl such as phenylacetamido; aryloxy ($C_{2-6}$) alkylamido such as phenoxyacetamido; or di ($C_{1-6}$) alkylamino such as dimethylamino. Suitable examples of $C_{1-6}$ alkyl include the methyl and ethyl groups.

Preferably the pyrimidinyl group $R^2$ is substituted by one or two groups selected from chloro, amino, acetamido and methyl.

Suitably $R^2$ is a pyrimidin-2-yl group. Suitably also $R^2$ is a pyrimidin-4-yl group. In one preferred aspect $R^2$ is a 4-substituted pyrimidin-2-yl group. In another preferred aspect $R^2$ is a 4,6-disubstituted pyrimidin-2-yl group.

A favoured group of compounds of this invention is that of the formula (II):

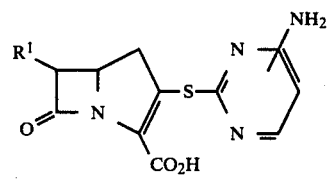

and pharmaceutically acceptable salts and in-vivo hydrolysable esters thereof wherein $R^1$ is as hereinbefore defined. Suitably the amino substituent is in the 5-position of the pyrimidinyl ring. Suitably also the amino substituent is in the 4-position of the pyrimidinyl ring.

A further favoured group of compounds of this invention is that of the formula (III):

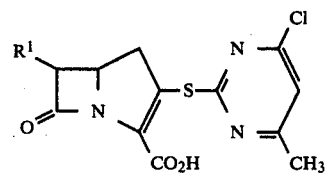

and pharmaceutically acceptable salts and in-vivo hydrolysable esters thereof wherein $R^1$ is as hereinbefore defined.

Another favoured group of compounds of this invention is that group analogous to formula (II) wherein amino is replaced by acetamido.

Suitably $R^1$ in the compounds of the formulae (I)–(III) is a hydrogen atom. Suitably $R^1$ in the compounds of the formulae (I)–(III) is a $CR^3R^4R^5$ group. Alternatively the group $R^1$ is an α-sulphonato-oxyethyl or α-sulphonato-oxypropyl group.

Suitably $R^3$ is a hydrogen atom or a hydroxy group. Suitably $R^5$ is a hydrogen atom or a methyl, ethyl, n-propyl or phenyl group. Suitably $R^4$ is a hydrogen atom or a methyl, ethyl or n-propyl group. Favourably $R^4$ is a hydrogen atom or a methyl group. Favourably $R^5$ is a hydrogen atom or a methyl group.

Favourably the $CR^3R^4R^5$ moiety is a —C(CH_3)_2OH, —CH(CH_3)OH or —CH(C_2H_5)OH group, of these the —CH(CH_3)OH group is preferred.

It is to be realised that compounds of the formulae (I) to (III) wherein $R^3$, $R^4$ and $R^5$ have different values may exist in either the 8R or 8S form (the C-8 carbon atom being that adjacent to the ring carbon). If desired these compounds may be presented as mixtures of the 8R and 8S forms.

The compounds of the formulae (I)–(III) may have the cis- or trans- configuration about the β-lactam ring, or they may be provided as mixtures thereof.

The compounds of the formulae (I)–(III) may have 5S or 5R stereochemistry or may be provided as mixtures thereof. It is believed that the more active isomer is that which exemplified in the relation for formula (I) has the configuration shown in formula (IV):

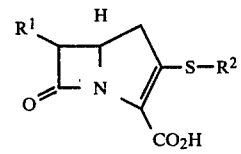

Suitable esters of the compounds of the formulae (I)–(IV) include those cleavable by biological methods and by chemical methods such as hydrogenolysis, hydrolysis electrolysis or photolysis.

Suitably the carboxylic acid is esterified by a group of the sub-formula (a), (b), (c), (d), (e) or (f):

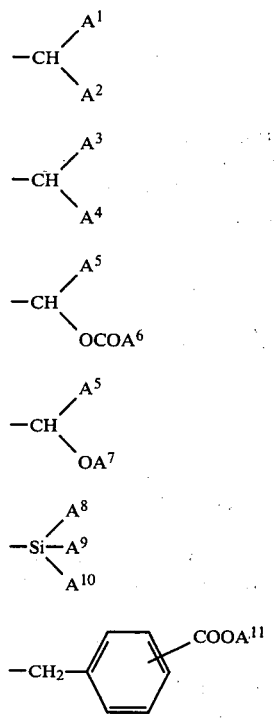

wherein $A^1$ is a hydrogen atom, $C_{1-6}$ alkanoyl or an alkyl, alkenyl or alkynyl group of up to 3 carbon atoms; $A^2$ is a hydrogen atom or a methyl group; $A^3$ is a phenyl group or a phenyl group substituted by a fluorine, chlorine or bromine atom or a nitro, methyl or methoxy group; $A^4$ is a hydrogen atom or a phenyl group or a phenyl group substituted by a fluorine, chlorine or bromine atom or a nitro, methyl or methoxy group; $A^5$ is a hydrogen atom or a methyl group; $A^6$ is a $C_{1-4}$ alkyl, phenyl or $C_{1-4}$ alkoxy group or $A^5$ is joined to $A^6$ to form a phthalidyl, dimethylphthalidyl or dimethoxyphthalidyl group; $A^7$ is a $C_{1-4}$ alkyl, phenyl, chlorophenyl or nitrophenyl group; $A^8$ is a $C_{1-4}$ alkyl or phenyl group; $A^9$ is a $C_{1-4}$ alkyl or phenyl group; $A^{10}$ is $C_{1-4}$ alkyl; and $A^{11}$ is $C_{1-4}$ alkyl: or $CHA^1A^2$ is a phenacyl or bromophenacyl group.

Favourably $A^1$ is a hydrogen atom or a methyl, ethyl, vinyl or ethenyl group. Favourably $A^2$ is a hydrogen atom. Favourably $A^3$ is a phenyl, p-bromophenyl, p-methoxyphenyl or p-nitrophenyl group. Favourably $A^4$ is a hydrogen atom. Favourably $A^6$ is a methyl, t-butyl or ethoxy group or is joined to $A^5$. Favourably $A^7$ is a methyl group.

Preferred groups of the sub-formula (a) include the methyl, ethyl and acetonyl groups.

Preferred groups of the sub-formula (b) include the benzyl and p-nitrobenzyl groups.

Preferred groups of the sub-formula (c) include the acetoxymethyl, pivaloyloxymethyl, α-ethoxycarbonyloxymethyl and phthalidyl groups.

A preferred group of the sub-formula (d) is the methoxymethyl group.

Preferred groups of the sub-formula (e) include the trimethylsilyl, tert-butyldimethylsilyl and tertbutyldiphenylsilyl groups.

A preferred group of the sub-formula (f) is p-methoxycarbonylbenzyl.

Particularly preferred esterifying groups are the p-nitrobenzyl and phthalidyl groups.

Pharmaceutically acceptable in-vivo hydrolysable esters are those esters which hydrolyse in the human body to produce the parent acid or its salt. Such esters may be identified by administration to a test animal such a rat or mouse by intravenous administration and thereafter examining the test animal's body fluids for the presence of the compound of the formula (I) or its salt.

Suitable esters of this type include those of sub-formula (c) as hereinbefore defined.

Suitable pharmaceutically acceptable salts include those of the alkali and alkaline earth metals, of these the sodium and potassium salts are preferred. These pharmaceutically acceptable salts may be formed at the C-2 carboxy and/or at the C-6 sulphonato-oxyethyl moiety (if present). Thus compounds of the formula (I) wherein $R^1$ contains a $OSO_3H$ group or pharmaceutically acceptable salt thereof, may be in the form of a di-salt such as the di-sodium or dipotassium salt, or may be in the form of a mono-salt of an in-vivo hydrolysable ester, or may be in the form of a monosalt of an acid or may be in the form of a di-acid.

Non-pharmaceutically acceptable salts of the compounds of the formula (I) are also of use as they may be converted to the compound of the formula (I) or a pharmaceutically acceptable salt or in-vivo hydrolysable ester thereof.

In a further aspect of this invention there is provided a pharmaceutical composition which comprises a compound of the formula (I) or pharmaceutically acceptable salt or in-vivo hydrolysable ester thereof and a pharmaceutically acceptable carrier.

The compositions of this invention may be prepared by conventional methods of preparing antibiotic compositions and in conventional manner may be adapted for oral, topical or parenteral administration.

Aptly, the compositions of this invention are in the form of a unit-dose composition adapted for oral administration.

Alternatively the compositions of this invention are in the form of a unit-dose composition adapted for administration by injection.

Unit dose forms according to this invention will normally contain from 50 to 500 mgs of a compound of this invention, for example about 62.5, 100, 125, 150, 200, 250 or 300 mgs. Such compositions may be administered from 1 to 6 times a day or more conveniently 2, 3 or 4 times a day so that the total daily dose for a 70 kg adult is about 200 to 2000 mgs, for example about 400, 600, 750, 1000 or 1500 mgs.

The compositions of this invention may be used to treat bacterial infection, in animals such as mammals including humans, for example infections of the respiratory tract, urinary tract or soft tissues, or mastitis in cattle.

The carriers used in the compositions of this invention may include diluents, binders, disintegrants, lubricants, colours, flavouring agents or preservatives in conventional manner. Thus suitable agents include lactose, starch, sucrose, calcium phosphate, sorbitol, polyvinylpyrrolidone, acacia, gelatin, tragacanth, potato starch or polyvinylpolypyrrolidone, magnesium stearate or sodium lauryl sulphate.

Orally administrable forms of the compositions of this invention are most suitably in the form of unit-dose units such as tablets or capsules.

The present invention also provides synergistic pharmaceutical compositions which comprise a pharmaceutical composition as hereinbefore described which also contains a penicillin or a cephalosporin.

Suitable penicillins for inclusion in the compositions of this invention include benzyl penicillin, phenoxymethylpenicillin, ampicillin or a pro-drug therefor, amoxycillin or a pro-drug therefor, carbenicillin or a pro-drug therefor, ticarcillin or a pro-drug therefor, suncillin, sulbenicillin, azlocillin or mezlocillin.

Particularly suitable penicillins for inclusion in orally administrable compositions of this invention include ampicillin and its orally administrable pro-drugs, amoxycillin and its orally administrable pro-drugs and orally administrable pro-drugs of carbenicillin. Thus particularly suitable penicillins include ampicillin anhydrate, amicillin trihydrate, sodium ampicillin, talampicillin hydrochloride, pivampicillin hydrochloride and bacampicillin hydrochloride; amoxycillin trihydrate, sodium amoxycillin; and the sodium salts of the phenyl and 5-indanyl α-esters of carbenicillin.

A preferred penicillin for inclusion in the orally administrable compositions of this invention is amoxycillin trihydrate. A further preferred penicillin for inclusion in the orally administrable compositions of this invention is ampicillin trihydrate.

Particularly suitable penicillins for inclusion in injectably administrable compositions of this invention include injectable salts such as the sodium salt of ampicillin, amoxycillin, carbenicillin and ticarcillin.

A preferred penicillin for inclusion in the injectably administrable compositions of this invention is sodium amoxycillin. A further preferred penicillin for inclusion in the injectably administrable compositions of this invention is sodium ampicillin.

Particularly suitable cephalosporins for inclusion in the compositions of this invention include cephaloridine, cephalexin, cephradine, cefazolin and cephalothin.

A particularly suitable cephalosporin for inclusion in the orally administrable compositions of this invention is cephalexin.

Particularly suitable cephalosporins for inclusion in the injectably administrable compositions of this invention include cephaloridine, cefazolin and cephradine, generally as their pharmaceutically acceptable salt.

The weight ratio between compound of this invention and penicillin or cephalosporin is generally from 10:1 to 1:10, more usually from 5:1 to 1:5 and normally from 3:1 to 1:3.

The penicillin or cephalosporin is generally utilised in its conventionally administered amount.

In another aspect the present invention provides a process for the preparation of a compound of the formula (I) which process comprises:

(a) the elimination of O=PR$^6$R$^7$R$^8$ in the ring-closing of an ester of the compound of the formula (V):

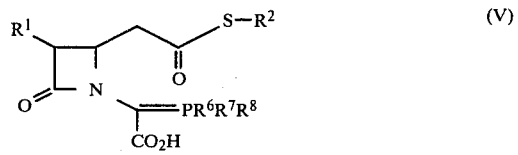

wherein R$^1$ and R$^2$ are as hereinbefore defined and R$^6$, R$^7$ and R$^8$ are independently phenyl or methoxyphenyl groups:

or (b) the reaction of a compound of the formula (VI)

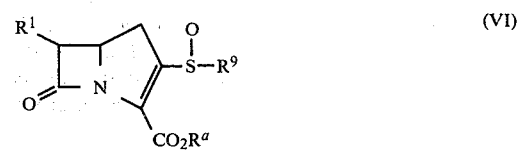

wherein R$^a$ is carboxy-blocking group or a hydrogen atom, and R$^9$ is an organic group bonded via a carbon atom and is different to the group R$^2$; and a compound of the formula (VII):

$$R^2-SH \qquad (VII)$$

or reactive derivative thereof, wherein R$^2$ is as hereinbefore defined;

or (c) the reaction of a compound of the formula (VIII):

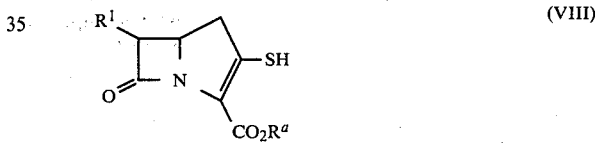

or reactive derivative thereof wherein R$^a$ is a carboxy-blocking group or hydrogen atom, and R$^1$ is as hereinbefore defined, with a compound of the formula (IX):

$$X-R^2 \qquad (IX)$$

wherein X is a displaceable group and R$^2$ is as hereinbefore defined;

or (d) the reaction of an ester of a compound of the formula (X):

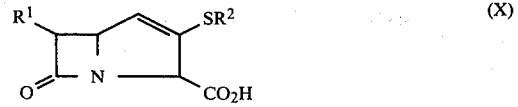

wherein R$^1$ and R$^2$ are as hereinbefore defined with a base capable of isomerising the double bond:
and thereafter if necessary:
(i) removing any carboxy-protecting group R$^a$,
(ii) converting the product into a pharmaceutically acceptable salt or in-vivo hydrolysable ester,
(iii) oxidising the sulpur atom to afford an SO group.

Suitable carboxyl-blocking derivatives for the group —CO$_R{^a}$ in formulae (VI) and (VII) include salts, esters, and anhydride derivatives of the carboxylic acid. The derivative is one which may readily be cleaved at a later stage of the reaction. The salts need not be pharmaceutically acceptable. Suitable salts include inorganic salts, for example metal salts such as silver or mercuric salt, or alkali metal salts such as the lithium or sodium salt, or tertiary amine salts, such as those with tri-lower-alkylamines, n-ethylpiperidine, and dimethylpiperazine. A preferred salt is with triethylamine.

Suitable ester-forming carboxyl-blocking groups are those which may be removed under conventional conditions. Such groups for $R^a$ include benzyl, p-methoxybenzyl, 2,4,6-trimethylbenzyl, 3,5-di-t-butyl-4-hydroxybenzyl, benzoylmethyl, p-nitrobenzyl, 4-pyridylmethyl, 2,2,2-trichloroethyl, 2,2,2-tribromoethyl, t-butyl, t-amyl-diphenylmethyl, triphenylmethyl, adamantyl, 2-benzyloxyphenyl, 4-methylthiophenyl, tetrahydrofur-2-yl, tetrahydropyran-2-yl, pentachlorophenyl, p-toluenesulphonylethyl, methoxymethyl, a silyl, stannyl or phosphorus-containing group, an oxime radical of formula —N=CHR° where R° is aryl or heterocyclic, or an in vivo hydrolysable ester.

The carboxyl group may be regenerated from any of the above esters by usual methods appropriate to the particular $R^a$ group, for example, acid—and base—catalysed hydrolysis, or by enzymically—catalysed hydrolysis, or by hydrogenation. The hydrolysis must of course be carried out under conditions to which the groups on the rest of the molecule are stable.

When it is desired to produce a compound of formula (I) in the form of a free acid or salt by the process of this invention, a compound of formula (VI) or (VIII) is generally employed wherein $R^a$ is a carboxyl-blocking group. For the preparation of a compound of formula (I) in the form of a pharmaceutically acceptable ester, it is convenient to employ a compound of formula (VI) or (VIII) wherein $R^a$ represents the desired ester group.

Preferably the process of this invention is performed on a compound of the formula (VI) or (VIII) wherein $R^a$ is an ester-forming group.

Process variant (a) is mormally performed by heating the ester of the compound of the formula (V) in an inert solvent, for example temperatures of 90° to 120° C. and more suitably 100° to 110° C. may be employed in a solvent such as toluene, preferably under substantially anhydrous conditions. If it is desired to form a compound of the formula (I) containing an amino group, it is preferred to perform process variant (a) on the corresponding nitrocompound and convert the nitro group to an amino group in conventional manner for example by hydrogenation.

Process variant (b) may be performed in any solvent that is substantially inert during the reaction, for example tetrahydrofuran, dimethylformamide, dioxan, hexamethyl phosphoramide, dimethoxyethane or dimethoxydiethyl ether. Of these solvents dimethylformamide is preferred. Alternatively we have found it useful to use a phase transfer catalyst. Particularly suitable phase transfer catalysts include tetra-n-butyl ammonium bromide, cetyl benzyldimethyl ammonium chloride and cetyltriethylammonium chloride; suitable solvents include halogenated water-immiscible solvents such as chloroform in the presence of water. The reaction is normally performed at ambient or a depressed temperature, for example 20° C. to −70° C., and preferably between 0° C. and −50° C. However when using a phase transfer catalyst it is preferably to conduct the reaction between 0° C. and ambient temperature. When the thiol of the formula (VII) is used the reaction is normally carried out in the presence of a base. Examples of such bases include sodium hydride, sodium hydroxide, sodium alkoxide such as the methoxide, ethoxide or butoxide, sodium amide, potassium hydroxide, potassium alkoxide such as the methoxide, ethoxide or butoxide, potassium. amide, and trialkylamines such as triethylamine and tri-n-propylamine. Of these triethylamine is preferred. Preferably the base is present in an amount of at least 0.9 equivalents, more preferably between 1.0 and 1.2 equivalents per mole of the thiol compound. Instead of using a base in the reaction a reactive derivative of the thiol may be used, preferably the reactive derivative is a salt of the thiol, in particular an alkali metal salt such as sodium or potassium. The amount of thiol compound of the formula (VII) or reactive derivative thereof is generally between 1.0 and 1.5 moles per mole equivalent of the compound of the formula (VI).

Suitably $R^9$ is an optionally substituted $C_{1-6}$ alkyl $C_{2-6}$ alkenyl, $C_{2-6}$ alkynyl, aryl $(C_{1-6})$ alkyl, $C_{2-6}$ alkanoyl, aryl $(C_{2-6})$ alkanoyl, arylcarbonyl, aryl, heterocyclyl, heterocyclyl $(C_{1-6})$ alkyl, heteroaryl $(C_{1-6})$ alkyl or heteroaryl group. Suitably the hetero atom or hetero atoms in the above named heteroaryl and/or heterocyclyl moieties are selected from 1 to 4 oxygen, nitrogen or sulphur atoms. Suitable optional substituents for $R^9$ include amino, alkanoylamino, mono- and di-alkylamino, hydroxy, alkoxy and carboxy and salts and esters thereof. Preferably $R^9$ is a $C_{1-6}$ alkyl, $C_{2-6}$ alkenyl, aryl, such as phenyl or heteroaryl group, any of such groups being optionally substituted. Favourably $R^9$ is methyl, ethyl, alkanoylaminoethyl such as acetamidoethyl, alkanoylaminoethenyl such as acetamidoethenyl, aminoethyl, phenyl, pyridyl or pyrimidyl.

Process variant (c) may be carried out in any solvent that is substantially inert during the reaction, for example tetrahydrofuran, dimethylformamide, dioxan, dimethoxyethane, dimethoxydiethyl-ether or hexamethyl-phosphoramide. Of these solvents dimethylformamide is preferred. When the thiol compound of the formula (II) is used, the reaction is normally carried out in the presence of an acid acceptor, for example a carbonate or bicarbonate such as anhydrous potassium carbonate. Alternatively we have found it useful to use a phase transfer catalyst. Particularly suitable phase transfer catalysts include tetrabutylammonium bromide and cetyl benzyl dimethyl ammonium chloride; suitable solvents include halogenated water-immiscible solvents such as chloroform and dichloromethane in the presence of an aqueous base such as aqueous sodium hydroxide. The reaction is normally performed at a nonextreme temperature, for example −30° C. to +60° C., more suitably −10° C. to +40° C. and preferably at ambient temperature.

Suitably X is a halo moiety such as bromo or chloro or is a sulphonate ester moiety such as tosylate or mesylate. Of these preferably X is a chloro or brommo moiety. Instead of using an acid acceptor in the reaction, a reactive derivative of the thiol may be used, preferably the reactive derivative is a salt of the thiol, in particular an alkali metal salt such as sodium or potassium.

Process variant (d) may be performed by treating the compound of the formula (IX) in a solvent such as dimethylformamide, dimethylsulphoxide, diethyl ether, tetrahydrofuran, dimethoxyethane or dichloromethane with a strong base such as di-isopropylamine, diazabicyclononene or diazabicycloundecene at a temperature of about 0° C. to 25° C.

Compounds of the formula (V) may be prepared via the methods of European Patent Application Publication Number 0008514 substituting the substituted pyrimidinyl group for the $R_1$ of the afore-mentioned specification.

Compounds of the formula (VI) may be prepared by methods of European Patent Application Publication Number 0002564.

Alternatively the compounds of the formula (VI) may be prepared by the S-oxidation of a compound of the formula (XI):

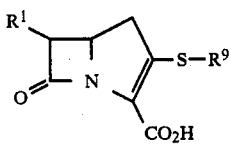

or salt or ester thereof wherein $R^1$ and $R^9$ are as defined in relation to formula (VI) with an oxidising agent; and thereafter if necessary converting the free acid or salt to an ester.

Suitable oxidising agents include perbenzoic acid, hydrogenperoxide, iodobenzene dichloride/water and sodium metaperiodate. Substituted perbenzoic acids such as m-chloroperbenzoic acid are preferred.

The reaction between the compund of the formula (X) and the oxidising agent is conveniently performed in an inert solvent such as methylene chloride, chloroform or carbon tetrachloride at an ambient or depressed temperature, preferably between −30° C. and +20° C.

The amount of the oxidising agent used in the oxidation of the compound of the formula (XI) can vary widely dependent on the type of oxidising agent, reaction conditions, presence of other potentially reactive groups, etc. Generally between 1 and 2 molar equivalents of the oxidising agent are preferred.

In a similar manner to the foregoing the compounds of the formula (I) wherein X is one may be prepared by the oxidation of a compound of the formula (I), Wherein X is zero.

The compounds of the formulae (VIII) (X) and (XI) may be prepared via the methods of European Patent Application Publications Nos. 0001627 and 0001628. Alternatively the compounds of the formula (VIII) may be prepared via the methods of European patent application No. 80302659.0 (Publication No. 24832).

The following Examples serve to illustrate the invention.

EXAMPLE 1 p-Nitrobenzyl (5R,6S)-3-[(4-chloro-6-methyl-pyrimid-2-yl)-thio]-6-[(S)-1-hydroxyethyl]-7-oxo-1-azabicyclo[3.2.0]-hept-2-ene-2-carboxylate

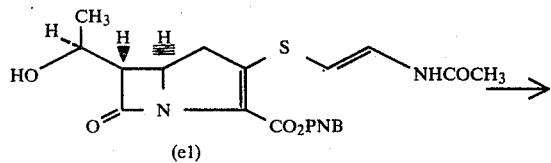

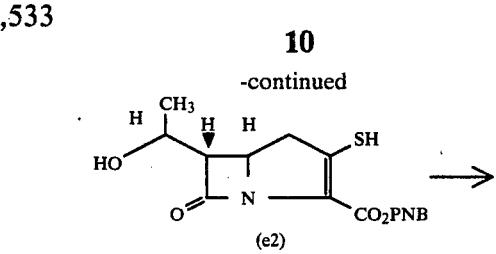

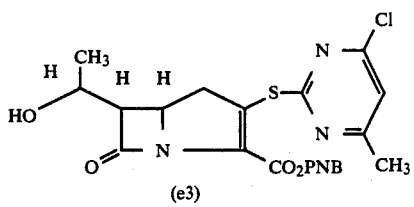

p-Nitrobenzyl (5R,6S)-3-[E-2-acetamidoethenylthio]-6-[(S)-1-hydroxyethyl]-7-oxo-1-azabicyclo[3.2.0]-hept-2-ene-2-carboxylate (e1) (500 mg; 1.119 mm) was dissolved in 1,4-dioxan (10 ml) containing water (30 drops). A solution of N-bromoacetamide (155 mg, 1.119 mm) in 1,4-dioxan (5 ml) was then added and the solution stirred at room temperature for 4.5 minutes. Chloroform (50 ml) was added and the organic phase was washed with pH 7.0, 0.05M phosphate buffer, saturated sodium chloride solution and dried over anhydrous magnesium sulphate. Filtration and removal of the solvent at reduced pressure yielded the crude thiol (e2) as a gum, $\nu_{max}$ (CHCl$_3$) 1780, 1730, 1700 cm$^{-1}$.

The crude thiol was dissolved in dry dimethyl formamide (10 ml) and stirred at room temperature for 25 minutes with anhydrous potassium carbonate (155 mg) and 2,4-dichloro-6-methylpyrimidine (182 mg; 1.119 mm). Ethyl acetate was added and the organic solution washed with water, saturated sodium chloride solution and dried over anhydrous magnesium sulphate. After filtration, the solvent was removed at reduced pressure to yield the crude product, which was chromatographed over silica gel (40 gm). Elution with 2% ethanol/chloroform afforded the title compound (e3) as a white solid. This solid was triturated with ethyl acetate/diethyl ether and collected by filtration (102 mg) $\nu_{max}$ (KBr) 3400, 1802, 1714, 1610, 1565, 1512, 1350, 1332 cm$^{-1}$, $\nu_{max}$ (EtOH) 326 nm (Em 14,530), 265 nm (Em 13,510), $\delta_H$ ($\delta_7$—DMF) 8.27 (2H, d, aromatic protons), 7.82 (2H, d, aromatic protons), 7.61 (1H, S, pyrimidine proton), 5.52 (2H, q, CH$_2$Ar), 5.23 L (1H, d, OH, exchanges with D$_2$O), 4.42 (1H, dt, 5-CH), 4.15 (1H, broad res., 8-CH), 3,1–3.8 (3H, t+ABX, 6-CH+4-CH$_2$), 2.48 (3H, s, pyrimidine CH$_3$), 1.31 (3H, d, CH$_3$CH), m/s (relative intensity %) 490.0703 (2) (C$_{21}$H$_{19}$N$_4$O$_6$SCl required 490.0710), 446(8), 407(38), 405(100), 361(10), 287(50), 286(40), 266(45), 160(45), 135(70), 107(60), 106(70).

EXAMPLE 2 p-Nitrobenzyl (5R, 6R)-3-[5-nitropyrimid-2yl)thio]-6-[(S)-1-hydroxyethyl]-7-oxo-1-azabicyclo[3.2.0]hept-2-ene-2-carboxylate

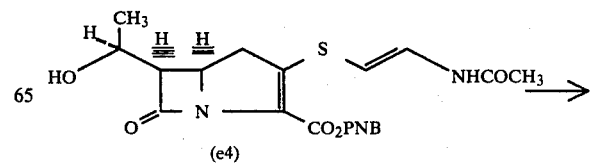

-continued

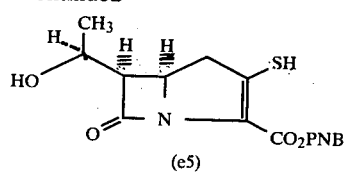

(e5)

↓

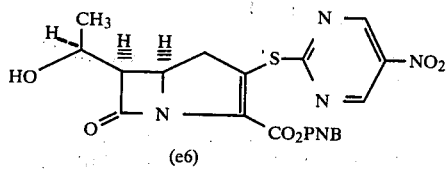

(e6)

p-Nitrobenzyl (5R, 6R)-3-[E-2-acetamidoethenyl-thio]-6-[(S)-1-hydroxyethyl]-7-oxo-1-azabicyclo[3.2.0-]hept-2-ene-2-carboxylate (e4) (250 mg; 0.56 mM) was dissolved in 1,4-dioxan (5 ml) containing water (15 drops). A solution of N-bromoacetamide (78.5 mg; 0.56 mM) in 1,4-dioxan (3 ml) was then added and the solution stirred at room temperature for 4.5 minutes. Chloroform (25 ml) was added and the organic phase was washed with pH 7.0, 0.05 M phosphate buffer, saturated sodium chloride solution and dried over anhydrous magnesium sulphate. Filtration and removal of the solvent at reduced pressure yielded the crude thiol (e5) as a gum. The thiol was then dissolved in chloroform (20 ml) and layered with water (15 ml). 2-Chloro-5-nitropyrimidine (180 mg; 1.119 mM), cetyl-dimethylbenzyl ammonium chloride (50 mg) and 0.1 N sodium hydroxide solution (5.6 ml; 0.56 mM) were added and the two phase system stirred vigorously at room temperature for 35 minutes. The mixture was diluted with dichloromethane (100 ml) and water (100 ml) and the organic layer washed with saturated sodium chloride solution, and dried over anhydrous magnesium sulphate. Filtration and removal of the solvent at reduced pressure gave the crude product, which was chromatographed over silica gel (15 gm). Elution with chloroform yielded the title compound (e6) as a yellow foam. Crystallisation from ethyl acetate/ether gave a bright yellow solid (75 mg), $\lambda_{max}$ (EtOH) 340 nm (Em 13850), 267 nm (Em 15810), $\nu_{max}$ (KBr) 3510 (broad), 1776, 1709, 1603, 1578, 1560, 1512, 1341, 1322 cm$^{-1}$, $\delta_H$ (CDCl$_3$) 9.27 (2H, s, pyrimidine protons), 8.22 (2H, d, aromatic protons), 7.63 (2H, d, aromatic protons), 5.38 (2H, q, CH$_2$Ar), 4.0-4.65 (2H, m, 5-CH+8-CH), 3.55-3.80 (3H, m, 4-CH$_2$+6-CH), 1.79 (1H, d, OH), 1.44 (3H, d, CH$_3$CH), m/e (relative intensity %) 443 (2), 401.0397 (5%, C$_{16}$H$_{11}$N$_5$O$_6$S requires 401.0430), 330 (5), 286 (25), 263 (15), 221 (16), 157 (30), 136 (45), 106 (70). 78 (100).

EXAMPLE 3

(5R, 6R)-3-[(5-aminopyrimide-2-yl)thio]-6-[(S)-1-hydroxyethyl]-7-oxo-1-azabicyclo[3.2.0]hept-2-ene-2-carboxylic acid

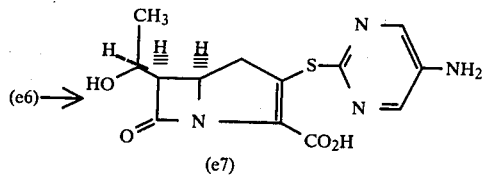

(e7)

A solution of the ester (e6) (15 mg) in 1,4-dioxan (5 ml), water (0.75 ml), ethanol (0.2 ml) and 0.05 M pH 7.0 phosphate buffer (1.0 ml) was hydrogenated in the presence of 10% palladium on carbon (23 mg) for 4 hours. The suspension was then filtered over Celite, washing well with water (25 ml). The filtrate was concentrated to approximately 20 ml and washed with ethyl acetate (3×25 ml). The resulting aqueous solution was estimated to contain 10.7 mg of the title compound (e7), based on Em 12,000 at $\lambda_{max}$ 305 nm in the u.v. spectrum, $\lambda_{max}$ (H$_2$O) 305 nm, 267 nm.

EXAMPLE 4

Preparation of 5(R,S), 6(S,R) p-nitrobenzyl-3(pyrimidine-2-sulphinyl)-6(1(R,S)-p-nitrobenzyloxycarbonyloxyethyl)-7-oxo-1-azabicyclo [3.2.0.]hept-2-ene-2-carboxylate

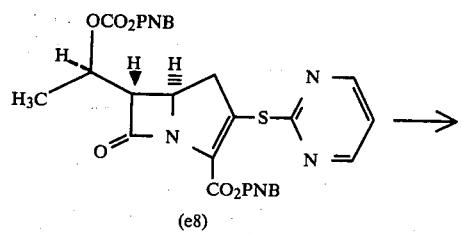

(e8)

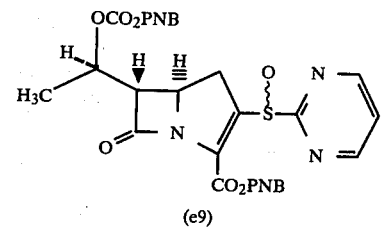

(e9)

5(R,S), 6(S,R) p-nitrobenzyl-3(pyrimidine-2-yl thio)-6-(1(R,S)-p-nitrobenzyloxycarbonyloxyethyl)-7-oxo-1-azabicyclo [3.2.0.]hept-2-ene-2-carboxylate (0.093 g) was dissolved in dry dichloromethane (100 ml) and treated with a solution of m-chloroperbenzoic acid (0.022 g) in dichloromethane at 0° C. The solution was stirred for 3 hours and allowed to warm to room temperature. The resulting colourless solution was washed three times with saturated sodium bicarbonate solution, dried over anhydrous mgnesium sulphate and conentrated under reduced pressure. The crude product was chromatographed on Merck Kieselgel 60 (<230 mesh) using ethyl acetate as eluant to afford a white foam (0.050 g, 53%) containing the sulphoxide as a 2:3 ratio of isomers.

$\lambda_{max}$ (EtOH) 264 nm; $\nu_{max}$ (CHCl$_3$) 1800, 1740, 1520 and 1350 cm$^{-1}$; $\delta$ (ppm, CDCl$_3$) major isomer: 1.45

(3H, d, J=7.5 Hz, —CH₃); 2.91 (1H, dd, J=19, 10 Hz, C₄—H); 3.40 (1H, dd, J=19, 10 Hz, C₄—H); 3.57 (1H, dd, J=3.5, 6Hz, C₆—H); 4.26 (1H, ddd, J=3.5, 10, 10 Hz, C₅—$_H$); 5.15 (1H, m, C₈—H); 5.23 (2H, s, C$\underline{H}$₂-Ar); 5.44 (2H, ABq, J=15Hz, C$\underline{H}$₂-Ar); 7.53-7.47 (3H, m, Ar-H and pyrimidine-H); 7.67-7.61 (2H, m, Ar-H); 8.26-8.20 (4H, m, Ar-H); 8.89 (2H, d, J=5Hz, pyrimidine-H) minor isomer: 1.45 (3H, d, J=7.5 Hz, —CH₃); 2.78 (1H, dd, J=18, 9 Hz, C₄—H); 3.42 (1H, dd, J=3.5, 6 Hz, C₆—H); 3.66 (1H, dd, J=18, 9 Hz, C₄—H); 4.41 (1H, ddd, J=3.5, 9, 9 Hz, C₅—H); 5.15 (1H, m, C₈—H); 5.23 (2H, S, CH₂—Ar); 5.42 (2H, ABq, J=15 Hz, C$\underline{H}$₂-Ar); 7.47-7.53 (3H, m, Ar-H and pyrimidine —H); 7.61-7.67 (2H, m, Ar-H); 8.20-8.26 (4H, m, Ar—H).

EXAMPLE 5

Preparation of 5(R,S), 6(S,R) p-nitrobenzyl-3(4-amino pyrimidine-2yl thio)-6(1(R,S) p-nitrobenzyloxycarbonyl oxyethyl)-7-oxo-1-azabicyclo [3.2.0]hept-2ene-2-carboxylate

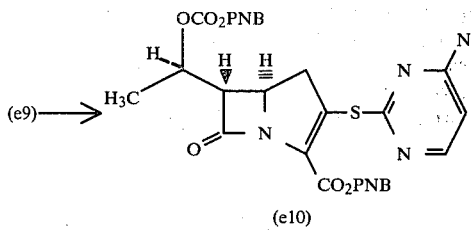

(e10)

The sulphoxide (e9) (0.015 g, as a mixture of isomers) was dissolved in dimethylformamide, cooled to −40° C. and treated with a solution of sodium-2-thiocytosine (0.005 g) in dimethylformamide and stirred for 40 minutes. The resultant solution was poured into excess ethyl acetate and washed five times with 3% sodium bicarbonate solution. The organic phase was dried over anhydrous magnesium sulphate, evaporated under reduced pressure and the residue chromatographed on Merck Kieselgel 60 ('230 mesh) using petrol (bp 60°-80°)/ethyl acetate as eluant to give the desired compound as a colourless oil (0.004 g, 27%), which could be crystallised from ethyl acetate to afford a white crystalline solid.

$\lambda_{max}$ (EtOH) 321 nm; $\nu_{max}$ (CHCl₃) 3510, 3400, 1780, 1730 1610, 1520, 1350 cm¹; δ (ppm, CDCl₃): 1.49 (3H, d, J=7Hz, C$\underline{H}$₃); 3.22 (1H, dd, J=9, 18 Hz, C₄-H); 3.42 (1H, dd, J=3, 7Hz, C₆—H); 3.81 (1H, dd, J=10, 18 Hz, C₄—$\underline{H}$); 4.27 (1H, ddd, J=3, 9, 9 Hz, C₅—H; 5.02 (2H, brs, —NH₂); 5.18 (1H, m, C₈—H); 5.26 (2H, S, CH₂—Ar); 5.40 (2H, ABq, J=14 Hz, CH₂Ar); 6.23 (1H, d, J=5 Hz, pyrimidine-H); 8.07 (1H, d, J=5 Hz, pyrimidine-H); 7.54 and 8.21 or 8.22 (4H, ABq, J=8.5 Hz, Ar-H); 7.63 and 8.21 or 8.22 (4H, ABq, J=8.5 Hz, Ar-H.

EXAMPLE 6

5(R,S), 6(S,R)-3(4-aminopyrimidine-2yl thio)-6(1R,S)-hydroxyethyl)-7-oxo-1-azabicyclo [3.2.0]hept-2-ene-2-carboxylate

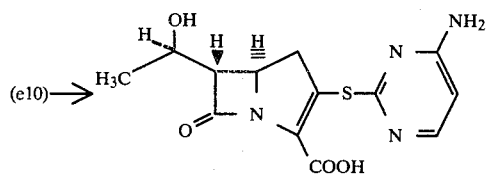

(e10)

The product from example 5 (e10; 0.020 g) was dissolved in 20% aqueous dioxan (20 ml) containing pH7 phosphate buffer (M/20, 2 ml) and 10% Pd/C (prehydrogenated, 0.020 g) and was hydrogenated at ambient temperature and pressure for two hours. The resultant solution was diluted with water (5 ml), filtered through Kieselguhr, the organic solvent evaporated and the aqueous solution extracted with ether (3×10 ml). Examination of the aqueous phase by UV showed it to contain the title compound (0.007 g, 75%).

$\lambda_{max}$ (H₂O) 300 nm.

The concentrations of this compound required to inhibit the growth of the following bacteria are given below:

| Organism | μg. ml⁻¹ (microtitre in broth) |
|---|---|
| Citrobacter freundii E8 | 12.5 |
| Enterobacter cloacae N1 | 3.1 |
| Escherichia coli 0111 | 1.6 |
| Escherichia coli JT39 | 0.8 |
| Klebsiella aerogenes A | 1.6 |
| Proteus mirabilis C977 | 1.6 |
| Proteus morganii 1580 | 1.6 |
| Proteus rettgeri WM16 | 6.2 |
| Proteus vulgaris W091 | 6.2 |
| Pseudomonas aeruginosa A | 100 |
| Salmonella typhimurium CT10 | 0.8 |
| Serratia marcescens US20 | 25 |
| Shigella sonnei MB 11967 | 1.6 |
| Bacillus Subtilis A | 0.4 |
| Staphylococcus aureus Oxford | 0.4 |
| Staphylococcus aureus Russell | 0.4 |
| Staphylococcus aureus 1517 | 6.2 |
| Streptococcus faecalis I | 1.6 |
| Streptococcus pneumoniae CN33 | ≦0.1 |
| Streptococcus pyogenes CN10 | ≦0.1 |
| Escherichia coli ESS | 0.8 |
| Escherichia coli JT20 R⁺ | 1.6 |
| Klebsiella aerogenes NA95 R⁺ | 1.6 |
| Pseudomonas aeruginosa Dalgliesh | 50 |

EXAMPLE 7

3(R,S),
4(S,R)-3(1(S,R)-p-nitrobenzyloxycarbonyloxyethyl)-1-
(1-p-nitrobenzyloxycarbonyl-1-triphenylphos-
phoranylidene methyl)-4-(4-acetamido pyrimidine-2yl
thiocarbonyl methyl)azetidine-2one

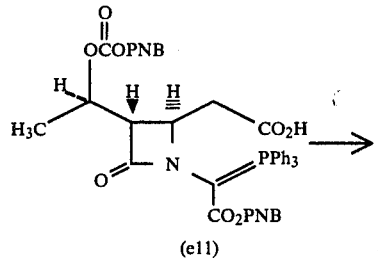

(e11)

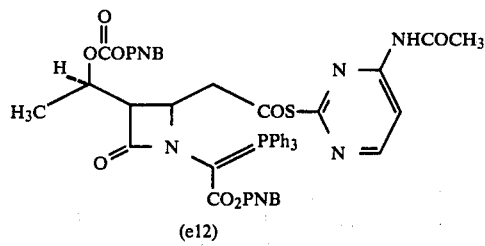

(e12)

(i) Preparation of lithium 4-acetamido pyrimidine-2yl thiolate

2-Thiocytosine (0.98 g) was refluxed in acetic anhydrous (10 ml) for 45 minutes. The resulting brown solution was cooled to form a precipitate which was filtered, washed with ethanol, and dried to give the desired compound in quantitative yield, $\nu_{max}$ (nujol) 3150, 1720, 1610 cm$^{-1}$. δ (ppm) 2.18 (3H, s, COCH$_3$); 3.40 (br, s, D$_2$O exch, S-H); 7.52 (1H, d, J=7 Hz, aromatic C-H); 7.96 (1H, d, J=5 Hz, aromatic C-H), 11.3 br.s, D$_2$O exch, N-H).

The product (0.50 g) was added to a stirred solution of lithium (0.020 g) in ethanol (10 ml) and the mixture stirred for 5 minutes. The solvent was evaporated to give a colourless gum which crystallised on trituration with ether to afford the lithium thiolate in quantitative yield.

(ii) Thio-ester formation

The acid (e11); (0.200 g) was dissolved in dry tetrahydrofuran (10 ml) and treated with triethylamine (0.025 g) followed by diethylphosphochloridate (0.050 g) in tetrahydrafuran (1 ml). The reaction was stirred at room temperature for 3 hours and treated with lithium 4-acetamido pyrimidine-2yl thiolate (0.060 g). The mixture was stirred for a further 45 minutes at room temperature, filtered and the solvent evaporated. The residue was dissolved in ethyl acetate (20 ml), washed with saturated sodium bicarbonae (3×10 ml) and the organic phase dried over anhydrous magnesium sulphate. The solvent was evaporated and the residue chromatographed on Merck kieselgel 60 (<230 mesh) using ethyl acetate as eluant, The product (e12) was obtained as a cream-coloured foam (0.140 g, 60%). $\nu_{max}$ (CHC$_3$) 1740, 1710, 1560, 1350 cm$^{-1}$.

EXAMPLE 8

4(R,S), 1(1-p-nitrobenzyloxycarbonyl-1-triphenyl
phosphoranylidene
methyl)-4-(4-acetamidopyrimidin-2yl-thiocarbonyl
methyl)azetidine-2one

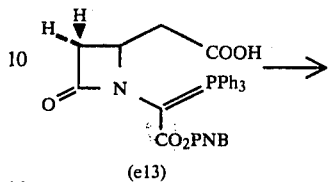

(e13)

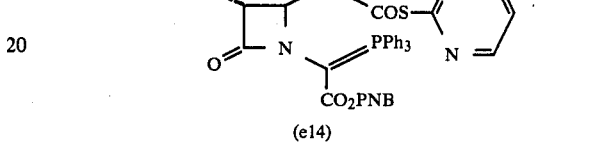

(e14)

The acid (e13; 0.190 g) was converted to the mixed phosphonic anhydride followed by treatment with lithium 4-acetamido pyrimidine-2yl thiolate (0.058 g) following the procedure described in example 7. After work-up the title compound (e14) was obtained as a colourless gum (0.091 g; 35%) which crystallised on trituration with ether.

$\nu_{max}$ (CHCl$_3$) 3150, 1735, 1720, 1560, 1350 cm$^{-1}$.

EXAMPLE 9

5(R,S),6(S,R) p-nitrobenzyl-3-(4-acetamido
pyrimidin-2-yl
thio)-6-(1(R,S)-p-nitrobenzyloxycarbonyl oxy
ethyl)-7-oxo-1-azabicyclo
[3.2.0.]hept-2-ene-2-carboxylate

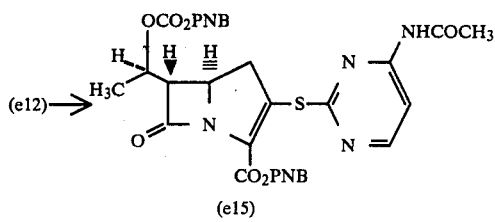

(e15)

The product from example 7 (e12; 0.024 g) was heated to reflux in dry toluene (25 ml) under an argon atmosphere for 3 hours. The solvent was evaporated and the residue chromatographed on Merck kieselgel 60 (<230 mesh) using petrol (bp 60°-80°)/ethyl acetate as eluant to yield the title compound (e15) (0.011 g, 65%) as a colourless oil, which was crystallised from petrol (bp 60°-80°)/ethylacetate. Mp. 138°-140° C. $\lambda_{max}$ (EtOH) 322 nm; $\nu_{max}$ (CHCl$_3$) 3400, 1785, 1740, 1720, 1560, 1350 cm$^{-1}$. δ(PPm, CDCl$_3$): 1.49 (3H,d,J=6 Hz, C$_8$—CH$_3$); 2.25 (3H,s,—COCH$_3$), 3.22 (1H, dd, J=9.5, 18 Hz, C$_4$—H); 3.46 (1H, dd, J=3, 7.5 Hz, C$_6$—H); 3.79 (1H, dd, J=9.5, 18 Hz, C$_4$—H), 4.31 (1H, ddd, J=3, 9.5, 9.5 Hz, C$_5$—H); 5.22 (1H, dq, J=6, 7.5 Hz, C$_8$—H), 7.54 and 8.21 or 8.23 (4H, ABq, J=7.5 Hz, Ar—H); 7.64 and 8.21 or 8.23 (4H, ABq, J=7.5 Hz, Ar—H), 7.94 (1H, d, J=6 Hz, pyrimidine-H); 8.44 (1H, d, J=6 Hz, pyrimidine-H).

EXAMPLE 10

5(R,S) p-nitrobenzyl-3(4-acetamido pyrimidin-2-yl thio)-7-oxo-1-azabicyclo [3.2.0] hept-2-ene-2-carboxylate

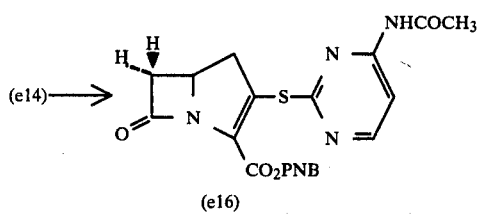

The product from example (8) (e14; 0.056 g) was heated to reflux in dry toluene (60 ml) following the procedure described in example (9). After work-up the title compound (e16) was obtained as a creamy-white solid (0.007 g, 20%).

$\lambda_{max}$ (EtOH) 322 nm, $\nu_{max}$ (CHCl$_3$) 3400, 1780, 1715, 1560 cm$^{-1}$.

EXAMPLE 11

5(R,S),6(S,R)-3(4-acetamido pyrimidin-2-yl thio)-6-(1(R,S)hydroxyethyl)-7-oxo-1-azabicyclo [3.2.0] hept-2-ene-2-carboxylate

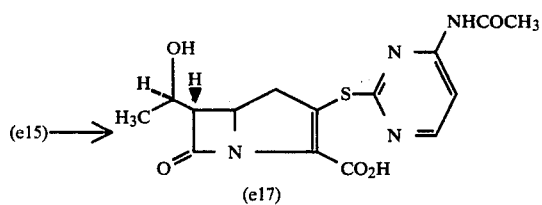

The product from example (9) (e15; 0.030 g) was treated as described in example 6. After work-up the title compound (e17) was obtained in aqueous solution (0.010 g, 63%) which was freeze-dried to a fluffy white solid. $\lambda_{max}$ (H$_2$O) 295 nm, $\nu_{max}$ (KBr) 3400, 1760, 1700, 1560, 1515 cm$^{-1}$.

δ(ppm, D$_2$O): 1.08 (3H, d, C$_8$—CH$_3$); 2.04 (3H, s, —COC$\underline{H}_3$); 2.85 (1H, dd, J=10, 18.5 Hz, C$_4$—H); 3.25 (1H, dd, J=10, 18.5 Hz, C$_4$—H), 3.29 (1H, dd, J=3, 7 Hz, C$_6$—H), 4.04 (1H, dq, J=6, 7 Hz, C$_8$—H); 4.11 (1H, ddd, J=3, 10, 10 Hz, C$_5$—H), 7.56 (1H, d, J=6 Hz, pyrimidine-H), 8.24 (1H, d, J=6 Hz, pyrimidine-H).

EXAMPLE 12

5(R,S)-3(4-acetamido pyrimidin-2-yl thio)-7-oxo-1-azabicyclo [3.2.0] hept-2-ene-2-carboxylate

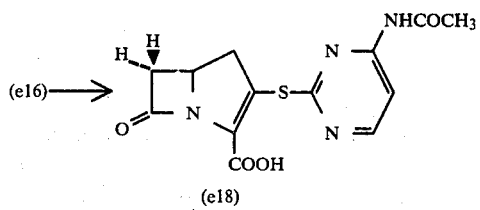

The product from example 10 (e16; 0.007 g) was treated as described in example 6. After work-up the title compound (e18) was obtained in aqueous solution (0.0085 g 17%). $\lambda_{max}$ (H$_2$O) 287 nm.

EXAMPLE 13

5(R,S), 6(S,R) p-nitrobenzyl-3 (4,6-diamino pyrimidin-2-yl thio)-6-(1(R,S) p-nitrobenzyloxycarbonyloxyethyl)-7-oxo-1-azabicyclo [3.2.0.]hept-2-ene-2-carboxylate

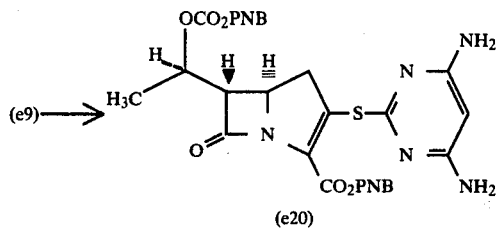

The sulphoxide (e9, 0.030 g) was treated with the sodium salt of 4,6-diamino-2-mercapto pyrimidine (0.010 g) following the procedure described in example 5. The title product (e20) was obtained as a colourless oil (0.007 g, 23%). $\lambda_{max}$325 nm, $\nu_{max}$ (CHCl$_3$) 3520, 3420, 1785, 1725, 1620, 1525, 1350 cm$^{-1}$. δ(ppm, CDCl$_3$): 1.49 (3H, d, J=7.5 Hz, C$_8$—CH$_3$); 3.22 (1H, dd, J=9, 18 Hz, C$_4'$—H); 3.40 (1H, dd, J=3, 8 Hz, C$_6$—H); 3.78 (1H, dd, J=9, 18 Hz, C$_4$—H); 4.23 (1H, ddd, J=3, 9, 9 Hz, C$_5$—H); 5.16 (1H, dq, J=7.5, 8 Hz, C$_8$—H); 5.25 (2H, S, CH$_2$Ar); 5.30 and 5.49 (2H, ABq, J=14 Hz, CH$_2$—Ar); 5,34 (1H, S, pyrimidine-H); 7.54 and 8.23 or 8.21 (4H, ABq, J=8.5 Hz, Ar—H); 7.64 and 8.23 or 8.21 (4H, ABq, J=8.5 Hz, Ar—H).

EXAMPLE 14

Tetra-n-butylammonium salt of p-nitrobenzyl (5R,6R)-6-[(S)-1-hydroxysulphonyloxyethyl]-3-(5-nitropyrimid-2-yl thio)-7l-oxo-1-azabicyclo [3.2.0]hept-2-ene-2-carboxylate

Step A

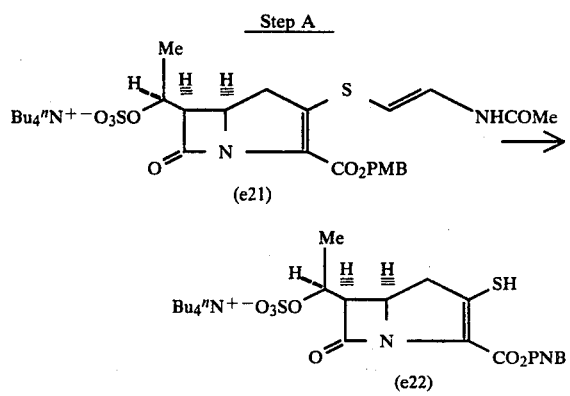

The tetra-n-butylammonium salt (e21) (200 mg) in 15% aqueous dioxan was treated with N-bromoacetamide (36 mg) in dioxan. After stirring at room temperature the solution was diluted with chloroform, and the organic layer was washed with pH7 buffer solution and dilute brine. Evaporation of the dried (MgSO$_4$) organic layer yielded the thiol (e22) as a foam (156 mg); $\nu_{max}$ CHCl$_3$ 1780 and 1705 cm$^{-1}$.

Step B (e22) ⟶

-continued
Step B

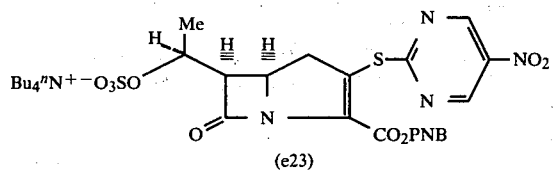

(e23)

A solution of the thiol (e22) and 5-nitro-2-chloropyrimidine (55 mg) in chloroform (5 ml) was stirred vigorously with an aqueous solution of sodium hydroxide (9 mg in 2.25 ml). After 40 min at room temperature, chloroform (30 ml) was added and the organic layer was washed with water (30 ml) and dried (MgSO$_4$). The solution was evaporated in vacuo and the residue was chromatographed on silica-gel using a gradient elution from chloroform to 20% ethanol in chloroform. Fractions containing the product were collected and evaporated in vacuo to afford the title compound (e23) as a gum (34 mg); $\lambda_{max}$ (EtOH) 336 and 267 nm; $\nu_{max}$ (CHCl$_3$) 1780 and 1725 cm$^{-1}$; $\delta$(CDCl$_3$) 0.99 (12H, t, J Hz, 4×CH$_3$CH$_2$CH$_2$), 1.43 (8H, m, 4×CH$_2$CH$_2$CH$_3$), 1.63 (11H, m, 4×CH$_2$CH$_2$CH$_3$ and CH$_3$CH), 3.25 (8H, m, 4×NCH$_2$CH$_2$), 3.52 (1H, dd, J 10.5 and 19.5 Hz, 4-CHa), 3,83 (1H, dd, J 5.5 and 11 Hz, 6-CH), 4.07 (1H, dd, J 19.5 and 9.5 Hz, 4-CHb), 4.51 (1H, dt, J, 5.5, 5.5 and 9.5 Hz, 5-CH), 4.85 (1H, m, CHCH$_3$), 5.28 and 5.50 (each 1H, d, J 14 Hz, CH$_2$C$_6$H$_4$NO$_2$), 7.65 and 8.22 (each 2H, d, J 9 Hz, C$_6$H$_4$NO$_2$) and 9.31 (2H, s, 2×pyrimidyl-CH).

EXAMPLE 15

Sodium (5R,6R)-3-(5-aminopyrimidyl-2-thio)-6-[(S) 1-hydroxysulphonyloxyethyl]-7-oxo-1-azabicyclo [3.2.0]hept-2-ene-carboxylate

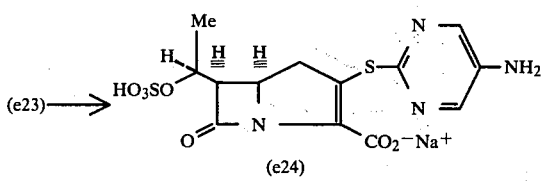

A mixture of the mono-ester (e23) (180 mg), 10% Pd on C (180 mg), dioxan (15 ml) water (5 ml) and 0.05 M pH7 phosphate buffer solution (5 ml) was shaken under hydrogen for 3.5 h. To the mixture was added a solution of sodium tetrafluoroborate (24 mg) in water (1 ml), before filtering over Celite washing well with water (40 ml). The solution was concentrated in vacuo to a volume of Ca 35 ml and was then washed with ethyl acetate (3×50 ml). The aqueous layer was further concentrated to small volume and then chromatographed on a column of Biogel P2 (3.5×25 cm) eluting with water. Fractions containing chromophores at $\lambda_{max}$ (H$_2$O) 304 and 268 nm in the u.v. spectrum were combined to afford an aqueous solution of the title compound (e24). A portion of the solution was freeze-dried to afford the product as a solid.

The concentrations of the compounds (e7) and e24) required to inhibit the growth of the following bacteria are given below:

| Organism | μg ml$^{-1}$ (microtitre in broth) | |
|---|---|---|
| | (e7) | (e24) |
| Citrobacter freundii E8 | 3.1 | 12.5 |
| Enterobacter cloacae N1 | 1.6 | 1.6 |
| Escherichia coli 0111 | 0.8 | 3.1 |
| Escherichia coli JT39 | 6.2 | 3.1 |
| Klebsiella aerogenes A | 0.8 | 1.6 |
| Proteus mirabilis C977 | 0.4 | 0.8 |
| Proteus morganii 1580 | 3.1 | 1.6 |
| Proteus rettgeri WM16 | 1.6 | 3.1 |
| Proteus vulgaris W091 | 1.6 | 3.1 |
| Pseudomonas aeruginosa A | 50 | >100 |
| Salmonella typhimurium CT10 | 0.8 | 3.1 |
| Serratia marcescens US20 | 6.2 | 6.2 |
| Shigella sonnei MB 11967 | 0.8 | (—) |
| Bacillus Subtilis A | 0.2 | 1.6 |
| Staphylococcus aureus Oxford | 0.2 | 3.1 |
| Staphylococcus aureus Russell | 0.4 | 3.1 |
| Staphylococcus aureus 1517 | 6.2 | 25 |
| Streptococcus faecalis I | 1.6 | 50 |
| Streptococcus pneumoniae CN33 | ≦0.1 | 0.8 |
| Streptococcus pyogenes CN10 | ≦0.1 | 0.4 |
| Escherichia coli ESS | 0.2 | 0.4 |

What we claim is:
1. A compound of the formula (I):

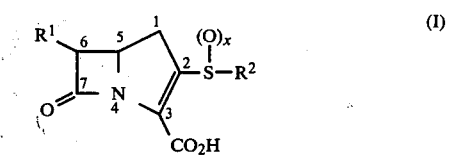

or a pharmaceutically acceptable salt or a pharmaceutically acceptable ester thereof that hydrolyzes in the human body to produce the free acid or salt wherein $R^1$ is hydrogen, α-sulphonato-oxyethyl. α-sulphonato-oxypropyl or is $CR^3R^4R^5$ wherein $R^3$ is hydrogen or hydroxy; $R^4$ is hydrogen or C$_{1-6}$ alkyl; and $R^5$ is hydrogen or C$_{1-6}$ alkyl, benzyl, or phenyl or is joined to $R^4$ to form together with the carbon atom to which they are joined a carbocyclic ring of 5 to 7 carbon atoms; $R^2$ is pyrimidinyl substituted by one, two or three groups selected from nitro, halo, amino, alkylamino of 1 to 6 carbon atoms in the alkyl moiety, alkylamido of 2 to 6 carbon atoms in the alkyl moiety, phenalkylamido wherein the alkyl moiety has 2 to 6 carbon atoms, phenoxyalkylamido wherein the alkyl moiety has 2 to 6 carbon atoms, and dialkylamino of 1 to 6 carbon atoms in each alkyl moiety, and in addition may be optionally substituted by one or two C$_{1-6}$ alkyl as the degree of substitution permits; and x is zero or one.

2. A compound according to claim 1 wherein said pyrimidinyl, $R^2$, is substituted by one or two groups selected from chloro, amino, acetamido and methyl, at least one of which being chloro, amino or acetamido.

3. A compound according to claim 1 wherein $R^2$ is a pyrimidin-2-yl group.

4. A compound according to claim 1 wherein $R^2$ is a pyrimidin-4-yl group.

5. A compound according to claim 1 of the formula (II):

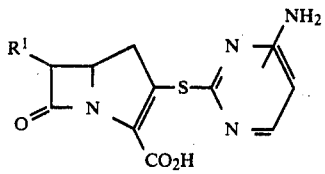

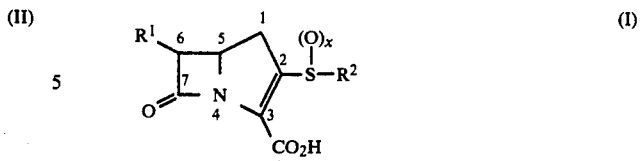

or a pharmaceutically acceptable salt or a pharmaceutically acceptable ester thereof that hydrolyzes in the human body to produce the free acid or salt, wherein $R^1$ is hydrogen, α-sulphonato-oxyethyl, α-sulphonato-oxypropyl or is $CR^3R^4R^5$ wherein $R^3$ is hydrogen or hydroxy; $R^4$ is hydrogen or $C_{1-6}$ alkyl; and $R^5$ is hydrogen or $C_{1-6}$ alkyl, benzyl, phenyl or is joined to $R^4$ to form together with the carbon atom to which they are joined a carbocyclic ring of 5 to 7 carbon atoms.

6. A compound according to claim 1 wherein $R^1$ is 1-hydroxyethyl.

7. A compound according to claim 1 selected from:
p-Nitrobenzyl (5R,6S)-3-[(4-chloro-6-methyl-pyrimid-2-yl)thio]-6-[(S)-1-hydroxyethyl]-7-oxo-1-azabicyclo[3.2.0]hept-2-ene-2-carboxylate;
p-nitrobenzyl (5R,6R)-3-[5-nitropyrimid-2-yl)thio]-6-[(S)-1-hydroxyethyl]-7-oxo-1-azabicyclo[3.2.0]hept-2-ene-2-carboxylate;
(5R,6R)-3-[(5-aminopyrimid-2-yl)thio]-6-[(S)-1-hydroxyethyl]-7-oxo-1-azabicyclo[3.2.0]hept-2-ene-2-carboxylic acid;
5(R,S), 6(S,R) p-nitrobenzyl-3(4-aminopyrimidin-2-yl thio)-6(1(R,S) p-nitrobenzyloxycarbonyloxyethyl)-7-oxo-1-azabicyclo[3.2.0]hept-2-ene-2-carboxylate;
5(R,S), 6(S,R)-3(4-aminopyrimidin-2-yl thio)-6(1-(R,S)-hydroxyethyl)-7-oxo-1-azabicyclo[3.2.0]hept-2-ene-2-carboxylate;
5(R,S),6(S,R) p-nitrobenzyl-3(4-acetamido pyrimidin-2-yl thio)-6(1(R,S)-p-nitrobenzyloxycarbonyloxyethyl)-7-oxo-1-azabicyclo[3.2.0]hept-2-ene-2-carboxylate;
5(R,S) p-nitrobenzyl-3(4-acetamido pyrimidin-2-yl thio)-7-oxo-1-azabicyclo[3.2.0]hept-2-ene-2-carboxylate;
5(R,S),6(S,R)-3(4-acetamido pyrimidin-2-yl thio)-6-(1-(R,S)hydroxyethyl)-7-oxo-1-azabicyclo[3.2.0]hept-2-ene-2-carboxylate;
5(R,S)-3(4-acetamido pyrimidin-2-yl thio)-7-oxo-1-azabicyclo[3.2.0]hept-2-ene-2-carboxylate;
5(R,S), 6(S,R) p-nitrobenzyl-3(4,6-diamino pyrimidin-2-yl thio)-6-(1(R,S) p-nitrobenzyloxycarbonyloxyethyl)-7-oxo-1-azabicyclo[3.2.0]hept-2-ene-2-carboxylate;
tetra-n-butylammonium salt of p-nitrobenzyl (5R,6R)-6-[(S)-1-hydroxysulphonyloxyethyl]-3-(5-nitropyrimid-2-ylthio)-7-oxo-1-azabicyclo[3.2.0]hept-2-ene-2-carboxylate;
sodium (5R,6R)-3-(5-aminopyrimidyl-2-thio)-6-[(S) 1-hydroxysulphonyloxyethyl]-7-oxo-1-azabicyclo[3.2.0]hept-2-ene-carboxylate.

8. A non-pharmaceutically acceptable salt of the formula (I)

wherein $R^1$ is hydrogen, α-sulphonato-oxyethyl, α-sulphonato-oxypropyl or is $CR^3R^4R^5$ wherein $R^3$ is hydrogen or hydroxy; $R^4$ is hydrogen or $C_{1-6}$ alkyl; and $R^5$ is hydrogen or $C_{1-6}$ alkyl, benzyl, phenyl or is joined to $R^4$ to form together with the carbon atom to which they are joined a carbocyclic ring of 5 to 7 carbon atoms; $R^2$ is pyrimidinyl substituted by one, two or three groups selected from nitro, halo, amino, alkylamino of 1 to 6 carbon atoms in the alkyl moiety, alkylamido of 2 to 6 carbon atoms in the alkyl moiety, phenalkylamido wherein the alkyl moiety has 2 to 6 carbon atoms, phenoxyalkylamido wherein the alkyl moiety has 2 to 6 carbon atoms, and dialkylamino of 1 to 6 carbon atoms in each alkyl moiety, and in addition may be optionally substituted by one or two $C_{1-6}$ alkyl as the degree of substitution permits; and x is zero or one.

9. A pharmaceutical composition useful for treating bacterial infections in mammals including humans which comprises an antibacterially effective amount of a compound of the formula (I):

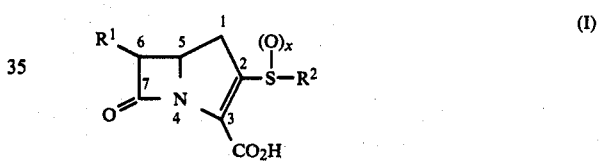

a pharmaceutically acceptable salt thereof or a pharmaceutically acceptable ester thereof that hydrolyzes in the human body to produce the free acid or salt, wherein $R^1$ is hydrogen, α-sulphonato-oxyethyl, α-sulphonato-oxypropyl or a group of the formula $CR^3R^4R^5$ wherein $R^3$ is hydrogen or hydroxy, $R^4$ is hydrogen or alkyl of 1-6 carbon atoms; and $R^5$ is hydrogen, alkyl of 1-6 carbon atoms benzyl or phenyl, or $R^5$ is joined to $R^4$ to form together with the carbon atom to which they are attached a carbocyclic ring of 5-7 carbon atoms; $R^2$ is pyrimidinyl substituted by one, two or three members selected from the group consisting of nitro, halo, amino, alkylamino of 1-6 carbon atoms in the alkyl moiety, alkylamido of 2-6 carbon atoms in the alkyl moiety, phenylalkylamido wherein the alkyl moiety has 2-6 carbon atoms phenoxyalkylamido of 2-6 carbon atoms in the alkyl moiety and dialkylamino of 1-6 carbon atoms in each alkyl moiety, or by one, two or three of said substituents and by one or two alkyl moieties of 1-6 carbon atoms as the degree of substitution permits; and x is zero or one, in combination with a pharmaceutically acceptable carrier.

10. A method of treating bacterial infections in mammals including humans which comprises administering to such a mammal in need thereof an antibacterially effective amount of a compound of the formula (I):

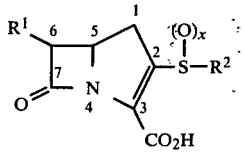
(I)

a pharmaceutically acceptable salt thereof or a pharmaceutically acceptable ester thereof that hydrolyzes in the human body to produce the free acid or salt, wherein $R^1$ is hydrogen, α-sulphonato-oxyethyl, α-sulphonato-oxypropyl or a group of the formula $CR^3R^4R^5$ wherein $R^3$ is hydrogen or hydroxy, $R^4$ is hydrogen or alkyl of 1-6 carbon atoms; and $R^5$ is hydrogen, alkyl of 1-6 carbon atoms, benzyl or phenyl, or $R^5$ is joined to $R^4$ to form together with the carbon atom to which they are attached a carbocyclic ring of 5-7 carbon atoms; $R^2$ is pyrimidinyl substituted by one, two or three members selected from the group consisting of nitro, halo, amino, alkylamino of 1-6 carbon atoms in the alkyl moiety, alkylamido of 2-6 carbon atoms in the alkyl moiety, phenalkylamido wherein the alkyl moiety has 2-6 carbon atoms, phenoxyalkylamido of 2-6 carbon atoms in the alkyl moiety and dialkylamino of 1-6 carbon atoms in each alkyl moiety, or by one, two or three of said substituents and by one or two alkyl moieties of 1-6 carbon atoms as the degree of substitution permits; and x is zero or one.

* * * * *